United States Patent [19]

Schechtman

[11] Patent Number: 5,026,589

[45] Date of Patent: Jun. 25, 1991

[54] DISPOSABLE SANITARY ARTICLES

[75] Inventor: Lee A. Schechtman, Fairfield, Ohio

[73] Assignee: The Procter & Gamble Company, Cincinnati, Ohio

[21] Appl. No.: 580,998

[22] Filed: Sep. 12, 1990

Related U.S. Application Data

[63] Continuation-in-part of Ser. No. 458,107, Dec. 28, 1989, abandoned.

[51] Int. Cl.$^5$ .................... A61F 13/15; A61F 13/46; B32B 5/22; B32B 5/24

[52] U.S. Cl. .................................... 428/138; 428/233; 428/252; 428/286; 428/311.7; 428/316.6; 428/317.9; 428/319.7; 604/370; 604/372; 604/378; 604/385.2

[58] Field of Search ............... 428/138, 233, 252, 286, 428/311.7, 316.6, 319.7; 604/370, 372, 378

[56] References Cited

U.S. PATENT DOCUMENTS

| | | | |
|---|---|---|---|
| 3,063,967 | 11/1962 | Schultz | 260/78.3 |
| 4,052,988 | 10/1977 | Doddi et al. | 128/335.5 |
| 4,337,181 | 6/1982 | Otey et al. | 523/128 |
| 4,372,311 | 2/1983 | Potts | 128/287 |

OTHER PUBLICATIONS

Remington's Pharmaceutical Sciences 15th Edition (1975), p. 1778, Mack Publishing Company, Easton, Pa.
R. S. Bezwada et al., Presented at the 197th National Meeting of the American Chemical Society, Dallas, Tex., Apr. 1989; Paper BTEC 29 (Abstract).
D. F. Williams et al., J. Appl. Polym. Sci., 1984, 29, 1865.
J. A. Ray et al., Surg. Gynecol. Obstet., 1981, 153, 497–507.
R. W. Hoile, Ann. R. Coll., Surg. Engl., 1983, 653, 168.
J. E. Blaydes et al., Opthalmic Surg., 1982, 13, 644.
Ibid., p. 1775.
Polylactones, 16, Cationic Polymerization of Trimethylene Carbonate and Other Cyclic Carbonates, Krichel-dorf and Jenssen, J. Macromol. Sci.-Chem., A26(4), pp. 631–644 (1989).
Polymerization and Ring Formation, III, Glycol Esters of Carbonic Acid.
Carothers and Van Natta; J. Am. Chem. Soc. 52, 314–26 (1930) (Abstract).
Ebulliometric Method for the Investigation of Polymerization Reactions, Heintz and Simon Naturwissenschaften 48, 160 (1961) (Abstract).

*Primary Examiner*—James C. Cannon
*Attorney, Agent, or Firm*—Jerry J. Yetter; Richard C. Witte; Thomas H. O'Flaherty

[57] ABSTRACT

Disposable sanitary garments comprise topsheet and/or backsheet materials prepared from polymers based on dioxanone. Diapers, sanitary napkins, pantiliners, and the like, prepared from the foregoing materials are disclosed.

8 Claims, No Drawings

DISPOSABLE SANITARY ARTICLES

CROSS-REFERENCE TO RELATED APPLICATION

This application is a Continuation-In-Part of U.S. patent application Ser. No. 458,107, filed Dec. 28, 1989.

TECHNICAL FIELD

The present invention relates to absorbent articles such as diapers, sanitary napkins, pantiliners, and the like, which are especially adapted for absorbing various bodily fluids. The articles herein are prepared from topsheet and/or backsheet and/or absorbent core materials which are designed to enhance their disposability, for example, by composting.

BACKGROUND OF THE INVENTION

A wide variety of absorbent structures designed to be efficient for the absorption of body fluids such as blood, urine, menses, and the like, are known. Disposable products of this type generally comprise some sort of fluid-permeable topsheet material, an absorbent core, and a fluid-impermeable backsheet material.

Heretofore, such absorbent structures have been prepared using, for example, topsheet materials prepared from woven, nonwoven, or porous formed-film polyethylene or polypropylene materials. Backsheet materials typically comprise flexible polyethylene sheets. Absorbent core materials typically comprise wood pulp fibers or wood pulp fibers in combination with absorbent gelling materials.

One aspect of such sanitary products which has recently been considered is their disposability. Although such products largely comprise materials which would be expected ultimately to degrade, and although products of this type contribute only a very small percentage of the total solid waste materials generated by consumers each year, nevertheless, there is currently a perceived need to devise such disposable products from materials which degrade relatively quickly, thereby lessening their bulk.

The practice of the present invention draws upon the wellknown teachings of the surgical arts to meet the aforesaid disposability issue. In particular, those aspects of the surgical arts relating to modern sutures and hemostats are employed in the practice of this invention to provide desirable topsheet, backsheet and absorbent core materials.

More particularly, the present invention employs a type of material used by surgeons in synthetic absorbable sutures to provide topsheet and backsheet materials which can be used to fashion diapers, sanitary napkins, pantiliners, and the like. Such suture materials, which are based on dioxanones, such as poly(1,3-dioxanone) and poly(p-dioxanone), as described hereinafter, are designed to degrade either enzymatically or by simple hydrolysis. The oxidized celluloses employed as absorbent cores herein are also well-known from surgical arts as absorbent hemostatic materials. Such materials are also broken down by natural biological processes, such as occur in composting processes, thereby enhancing their disposability.

In short, the present invention uses conventional knowledge from the medical arts relating to absorbable, hydrolyzable and otherwise degradable surgical materials, and reapplies such materials in an unconventional way to prepare sanitary products for use by the consumer.

BACKGROUND ART

The present invention relates to the preparation of diapers, sanitary napkins, pantiliners, and the like, all of which have been described in great detail in patents and other literature. A wide variety of such articles are commercially available. It is to be understood that this invention does not relate to the manufacture of any particular type, shape or style of such articles; rather, the invention herein relates to the particular choice of topsheet, backsheet and core materials which can be used in the manufacture of such articles to make them more disposable.

The preparation of surgical sutures from degradable polymers is described in REMINGTON'S PHARMACEUTICAL SCIENCES 15th Edition (1975) p. 1778, Mack Publishing Company, Easton, Pa.

The preparation of oxidized cellulose for use as absorbable surgical hemostats is described ibid., p. 1775.

The preparation and use of suture materials based on poly(p-dioxanone) is described in: R. S. Bezwada et al Presented at the 197th National Meeting of the American Chemical Society, Dallas, TX, April, 1989; paper BTEC 29; D. F. Williams et al J. Appl. Polym. Sci. 1984, 29, 1865; N. Doddi et al U.S. Pat. No. 4,052,988 (1977); J. A. Ray et al Surg. Gynecol. Obstet. 1981, 153, 497–507; W. Hoile, Ann. R. Coll. Surg. Engl. 1983, 65(3), 168; and J. E. Blaydes et al, Opthalmic Surg. 1982, 13, 644.

SUMMARY OF THE INVENTION

The present invention encompasses disposable absorbent structures, comprising a water-permeable topsheet, an absorbent core, and a water-impermeable backsheet, said structures being characterized in that said backsheet comprises a flexible film comprising a dioxanone-based polymer. Said polymer backsheet can also comprise glycolic acid and/or lactic acid moieties as a co-polymer with said dioxanone moieties.

The invention also encompasses disposable absorbent structures, comprising said water-permeable topsheet, absorbent core and water-impermeable backsheet, said structures being characterized in that said topsheet comprises a flexible porous sheet or woven or nonwoven web of polymer comprising the aforesaid dioxanone-based polymer. Again, the polymer topsheet can also comprise lactic acid and/or glycolic acid moieties, i.e., a co-polymer. Such topsheets are preferably in the form of a nonwoven web.

Other structures according to this invention are those wherein both the topsheet and the backsheet comprise the foregoing polymers, or co-polymers. Still other structures have both topsheet and backsheet prepared from the foregoing polymers, and also have oxidized cellulose (typically, with at least 16% carboxyl groups) comprising the absorbent core. The oxidized cellulose absorbent core can also contain an absorbent gelling material to provide additional absorbent capacity.

Structures according to any of the foregoing embodiments of the invention are provided in the form of disposable diapers, sanitary napkins or pantiliners.

All ratios, proportions and percentages herein are by weight, unless otherwise specified.

DETAILED DESCRIPTION

The polymers used to prepare the topsheet and backsheet materials employed herein are based on "dioxanone" which exists both as 1,4-dioxanone (referred to herein for simplicity as "p-dioxanone") of the formula

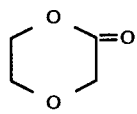

and as 1,3-dioxanone (sometimes referred to in the literature as "trimethylene carbonate") of the formula

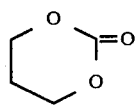

The use of 1,3-dioxanone for preparing bioabsorbable suture materials is well known. See, for example, U.S. Pat. No. 4,705,820; CA108(18)156502Z; CA112(18)164921h; and CA112(26)24055h. A general process for the olymerization of cyclic esters appears in U.S. Pat. No. 3,190,858. It is to be understood that both the 1,3-dioxanone and p-dioxanone isomers, and mixtures thereof, can be employed herein, according to the desires of the formulator. In either case, the dioxanone monomer is polymerized in art-disclosed fashion (e.g., metal catalysts, and the like) to provide the polymer having repeating units of the type (for p-dioxanone)

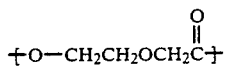

and of the type

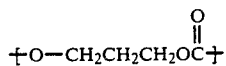

(for 1,3-dioxanone) with overall molecular weights ranging from several thousand to several million. Such polymers can be prepared in sheet form, or are available in fiber form, e.g., from Ethicon, Inc., under the trade name "PDS". The poly(glycolide-cotrimethylene cerborate) suture material is marketed by American Cyanamid under the name of "MAXON".

In an alternate mode, the dioxanone can be co-polymerized with materials such as glycolic acid (HOCH$_2$COOH), or its cyclic glycolide, or lactic acid (CH$_3$CHOHCOOH), or its cyclic lactide, to provide polymers whose degradation rates are somewhat faster than the homo-polymer comprising the dioxanone. Typically, such copolymers comprise 5-25% (mole basis) of the glycolic acid-based or lactic acid-based moieties.

It will be appreciated by the manufacturer of articles of the present type that the dioxanone-based polymers offer several advantages over homo-polymers based on glycolic acid or lactic acid, although such homo-polymers are known as degradable materials. First, the dioxanone-based polymers are easier to generate as monofilaments, which makes the formation of fibrous topsheets simpler. Second, the dioxanone-based polymers are more stretchable (i.e., exhibit a higher "elongation to break" parameter) than glycolate homopolymers, and are easier to handle on the high speed manufacturing equipment used in the disposables industry. Moreover, the dioxanone-based polymers are more flexible than the glycolate- or lactate-based polymers, which is an important consideration to the fit and comfort of disposable articles of the present type.

For use as topsheet materials, the foregoing dioxanone-based polymers can be cast or pressed as sheets having a multiplicity of perforations therethrough, or can be used in the form of filaments to prepare a woven or nonwoven web. The formation of perforated sheets and webs for use as topsheets is well-known in the art. The same manufacturing principles apply when such sheet or webs are made using the polymers herein.

For use as backsheet materials, the aforesaid dioxanone polyesters are simply cast or pressed into nonperforate, flexible sheets (typically 0.01 mm to 2 mm thickness).

It is to be understood that the articles herein can comprise either the topsheet, the backsheet, or both, made from the aforementioned dioxanone-based polyester polymers.

The oxidized cellulose absorbent material can be prepared by the mild oxidation of any convenient source of cellulose, e.g., wood pulp, cotton, and the like. Oxidized cotton is available from Parke-Davis in the form of gauze, strips and pads. Typically, the oxidized cellulose contains at least 16% (generally 16-24%) carboxyl groups.

It is to be understood that the articles herein can be prepared using either oxidized cellulose or ordinary cellulose fibers as the absorbent core. Moreover, said cores can also contain additional absorbent materials, especially the high fluid capacity absorbent gelling materials commonly used in modern diapers and sanitary napkins. Such materials include, for example, acrylates, starch grafted alkylates, and various gums and/or saccharidic gelling materials which absorb and hold 10–50 times their weight of water. Such materials are thoroughly described in the voluminous patent literature relating to disposable sanitary products, and are available from various commercial sources.

The following Examples illustrate the practice of this invention.

EXAMPLE I

A disposable baby diaper according to this invention is prepared as follows. The dimensions listed are for a diaper intended for use with a child in the 6–10 kilogram size range. These dimensions can be modified proportionately for different size children, or for adult incontinence briefs, according to standard practice.

1. Backsheet: 0.025–0.070 mm poly(p-dioxanone) film; width at top and bottom 33 cm; notched inwardly on both sides to a width-at-center of 28.5 cm; length 50.2 cm.

2. Topsheet: nonwoven fabric scrim comprising poly(p-dioxanone) fibers; width at top and bottom 33 cm; notched inwardly on both sides to a width-at-center of 28.5 cm; length 50.2 cm.

3. Absorbent core: oxidized cellulose (16–24% carboxyl); 8.4 mm thick, calendered; width at top and bottom 28.6 cm; notched inwardly at both sides to a width-at-center of 10.2 cm; length 44.5 cm.

4. Elastic leg bands: four individual rubber strips (2 per side); width 4.77 mm; length 370 mm; thickness 0.178 mm (all the foregoing dimensions being in the relaxed state).

The diaper of Example I is prepared in standard fashion by positioning the core material covered with the topsheet on the backsheet and gluing.

The elastic bands (designated "inner" and "outer", corresponding to the bands closest to, and farthest from, the core, respectively) are stretched to ca. 50.2 cm and positioned between the topsheet/backsheet along each longitudinal side (2 bands per side) of the core. The inner bands along each side are positioned ca. 55 mm from the narrowest width of the core (measured from the inner edge of the elastic band). This provides a spacing element along each side of the diaper comprising the flexible topsheet/backsheet material between the inner elastic and the curved edge of the core. The inner bands are glued down along their length in the stretched state. The outer bands are positioned ca. 13 mm from the inner bands, and are glued down along their length in the stretched state. The topsheet/backsheet assembly is flexible, and the glued-down bands contract to elasticize the sides of the diaper.

EXAMPLE II

A lightweight pantiliner suitable for use between menstrual periods comprises a pad (surface area 117 cm$^2$; SSK air felt 3.0 g) containing 1.0 g of absorbent gelling material particles (commercial polyacrylate; Nippon Shokubai); said pad being interposed between a porous formed-film topsheet according to U.S. Pat. No. 4,463,045 and a backsheet which comprises a 0.03 mm thickness p-dioxanone/glycolide co-polymer (85:15 mole basis) film.

EXAMPLE III

A catamenial product in the form of a sanitary napkin having two flaps extending outward from its absorbent core is prepared using a pad in the manner of Example II (surface area 117 cm$^2$; 8.5 g SSK air felt), per the design of U.S. Pat. No. 4,687,478, Van Tillburg, August, 1987. The backsheet comprises 0.025 mm polyethylene, and the topsheet comprises a nonwoven scrim of poly(p-dioxanone) fibers.

EXAMPLE IV

The sanitary napkin of Example III is modified by replacing the topsheet with a porous nonglossy formed film, per U.S. Pat. No. 4,687,478, said film being prepared from a poly(p-dioxanone)/lactide copolymer (90:10 mole ratio).

EXAMPLE V

A diaper is prepared according to Example I, but with the backsheet comprising poly-1,3-dioxanone in place of poly(p-dioxanone).

EXAMPLE VI

The napkin of Example III is modified by replacing the topsheet with a nonwoven scrim of poly(1,3-dioxanone) fibers.

It will be appreciated that the polymer materials herein can, if desired, be physically modified by means of various plasticizer materials, in well-known fashion. Likewise, various polyols and/or compounds containing carboxyl/hydroxyl moieties can be included in the polymerization mixture to modify the polymer properties, according to the desires of the formulator. Monomers such as caprolactone and the aforementioned lactic and glycolic acids are specific, but nonlimiting, examples of such materials. So long as the 1,3- or 1,4-dioxanone portion of the polymer remains at least about 35% (mole basis), preferably at least about 50% (mole basis) of the resulting polymer, the desired benefits of this invention can be achieved.

What is claimed is:

1. A disposable absorbent structure, comprising a water-permeable topsheet, an absorbent core, and a water-impermeable backsheet, said structure being characterized in that said backsheet comprises a flexible film comprising a dioxanone-based polymer.

2. A structure according to claim 1 wherein the polyester backsheet comprises a co-polymer based on dioxanone and a member selected from the group consisting of glycolic acid or glycolide and lactic acid or lactide.

3. A disposable absorbent structure, comprising a water-permeable topsheet, an absorbent core and a water-impermeable backsheet, said structure being characterized in that said topsheet comprises a flexible porous sheet or woven or nonwoven web of polymer comprising a dioxanone-based polymer.

4. A structure according to claim 3 wherein the topsheet comprises a co-polymer based on dioxanone and a member selected from the group consisting of lactic acid or lactide and glycolic acid or glycolide.

5. A structure according to claim 3 wherein the topsheet is in the form of a nonwoven web.

6. A disposable absorbent structure according to claim 1 comprising a water-permeable topsheet, a water-impermeable backsheet, and an absorbent core, said structure being characterized in that said absorbent core comprises oxidized cellulose.

7. A disposable absorbent structure according to claim 3 comprising a water-permeable topsheet, a water-impermeable backsheet, and an absorbent core, said structure being characterized in that said absorbent core comprises oxidized cellulose.

8. A structure according to claim 1 wherein both the topsheet and the backsheet comprise a dioxanone-based polymer.

* * * * *